US008773143B2

(12) United States Patent
Ledermann

(10) Patent No.: US 8,773,143 B2
(45) Date of Patent: Jul. 8, 2014

(54) METHOD AND CONTROL UNIT FOR MONITORING CABLE FAULTS ON A BROADBAND LAMBDA PROBE

(75) Inventor: Bernhard Ledermann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 237 days.

(21) Appl. No.: 13/472,594

(22) Filed: May 16, 2012

(65) Prior Publication Data

US 2012/0293183 A1 Nov. 22, 2012

(30) Foreign Application Priority Data

May 18, 2011 (DE) .......................... 10 2011 076 033
Jun. 8, 2011 (DE) .......................... 10 2011 077 171

(51) Int. Cl.
*G08B 21/00* (2006.01)
*B60Q 1/00* (2006.01)
*F02D 41/00* (2006.01)
*G01N 27/406* (2006.01)
*G01R 31/02* (2006.01)
*F02B 39/16* (2006.01)
*F02D 41/14* (2006.01)
*G01N 27/416* (2006.01)
*G01N 27/407* (2006.01)

(52) U.S. Cl.
CPC .......... *G01N 27/4065* (2013.01); *G01R 31/025* (2013.01); *F02B 39/16* (2013.01); *F02D 41/1455* (2013.01); *F02D 41/1494* (2013.01); *G01N 27/4163* (2013.01); *G01N 27/407* (2013.01)
USPC ............ 324/543; 340/635; 340/438; 123/679

(58) Field of Classification Search
CPC .......... G01N 27/4065; G01N 27/4163; G01N 27/407; G01R 31/025; F02B 39/16; F02D 41/1455; F02D 41/1494
USPC .................... 324/543; 340/635, 438; 123/679
See application file for complete search history.

(56) References Cited

U.S. PATENT DOCUMENTS 6,034,610 A * 3/2000 Schnaibel et al. ............ 340/635

FOREIGN PATENT DOCUMENTS

DE 102006061565 7/2008
WO 2009135862 11/2009

* cited by examiner

*Primary Examiner* — Jermele M Hollington
*Assistant Examiner* — Farhana Hoque
(74) *Attorney, Agent, or Firm* — Michael Best & Friedrich LLP

(57) ABSTRACT

A method for identifying cable faults at the terminals of a broadband lambda probe comprising a Nernst cell and a pump cell in the exhaust gas duct of an internal combustion engine. The broadband lambda probe has a reference electrode terminal RE, an internal pump electrode terminal IPE and an external pump electrode terminal APE. A pump current is applied to the broadband lambda probe and a pulsed reference pump current is applied to the broadband lambda probe. Cable faults are identified by the evaluation of potential swings in current.

18 Claims, 2 Drawing Sheets

METHOD AND CONTROL UNIT FOR MONITORING CABLE FAULTS ON A BROADBAND LAMBDA PROBE

BACKGROUND

The invention relates to a method for identifying cable faults at the terminals of a broadband lambda probe comprising a Nernst cell and a pump cell in the exhaust gas duct of an internal combustion engine, wherein the broadband lambda probe has a reference electrode terminal RE, an internal pump electrode terminal IPE and an external pump electrode terminal APE, wherein, via a control unit, a pump current is applied to the broadband lambda probe by means of a pump current source SQ and a pulsed reference pump current is applied to the broadband lambda probe by means of a reference current source SQr, wherein the pump current source SQ and the reference current source SQr are mutually connected to the terminals of the broadband lambda probe, a grounding resistor $R_{GND}$ and a reference voltage source $U_{Ref}$ with the aid of a first switching matrix and wherein the first switching matrix enables at least the switching connections Z_1: $R_{GND}$ with IPE and APE with SQ
Z_2: $R_{GND}$ with APE and IPE with SQ
Z_0: IPE with VM
Z_Rie: RE with SQr and IPE with VM.

The invention furthermore relates to a control unit for operating a broadband lambda probe comprising a Nernst cell and a pump cell in the exhaust gas duct of an internal combustion engine and for detecting information about the operating state of the broadband lambda probe, wherein the broadband lambda probe has as terminals a reference electrode terminal RE, an internal pump electrode terminal IPE and an external pump electrode terminal APE, wherein the control unit is connected to the terminals of the broadband lambda probe and a grounding resistor $R_{GND}$ and a calibration resistor $R_{ea}$ wherein the control unit has a first switching matrix for mutually connecting a pump current source SQ and a reference current source SQr to the terminals of the broadband lambda probe, the grounding resistor $R_{GND}$, the calibration resistor $R_{cal}$ and a reference voltage source $U_{Ref}$ wherein the control unit has a second switching matrix for mutually connecting the terminals of the broadband lambda probe, the grounding resistor $R_{GND}$ and the calibration resistor $R_{cal}$ and the pump current source SQ and the reference current source SQr to a digital measuring system DMS, and wherein the first switching matrix provides at least the following switching connections:

Z_1: $R_{GND}$ with IPE and APE with SQ
Z_2: $R_{GND}$ with APE and IPE with SQ
Z_0: IPE with VM
Z_Rie: RE with SQr and IPE with VM.

Legal regulations prescribe the monitoring of the composition of the exhaust gas of internal combustion engines for compliance with limit values. For this purpose, in the exhaust gas, by means of regulated three-way catalytic converters, undesirable substances such as nitrogen oxides and carbon monoxide are converted into substances that can be regarded as noncritical, such as water vapor, carbon dioxide and nitrogen. This conversion presupposes that the air-fuel mixture fed to the internal combustion engine is in a specific composition range around a stoichiometric composition. The latter is designated by the parameter lambda=1. The composition of the air-fuel mixture is monitored by exhaust gas sensors provided in the exhaust gas duct of the internal combustion engines, for example in the form of broadband lambda probes, which determine the oxygen partial pressure. The correct function of the exhaust gas sensors, and in particular also the ageing resistance thereof, are greatly dependent on the electronic circuitry interconnection thereof. The function blocks of such a circuitry interconnection are described by way of example in the document DE 10 2006 061 565 A1.

The document DE 10 2008 001697 A1 in the name of the present applicant describes an improved circuitry interconnection that allows—in addition to the operation of the exhaust gas sensor—information about the operating state of the broadband lambda probe used there as exhaust gas sensor to be detected, stored and forwarded to a superordinate engine controller via a digital interface. This arrangement enables a diagnosis of the cable connections between the circuitry interconnection and the broadband lambda probe with respect to short circuit and interruption and also with respect to compliance with the voltages permissible at the terminals. The operational availability of the exhaust gas probe can be detected and the electrode polarization thereof and the ageing can be continuously monitored.

The as yet unpublished document R.330560 in the name of the present inventor describes a device for operating a broadband lambda probe in the exhaust gas duct of an internal combustion engine and for detecting information about the operating state of the broadband lambda probe, wherein the broadband lambda probe has as terminals a reference electrode terminal RE, an internal pump electrode terminal IPE, an external pump electrode terminal APE and a measurement terminal MES, wherein the device is connected to the terminals of the broadband lambda probe and a grounding resistor $R_{GND}$ and a calibration resistor $R_{cal}$, wherein the device has a first switching matrix for mutually connecting a pump current source SQ and a reference current source SQr to the terminals of the broadband lambda probe, the grounding resistor $R_{GND}$, the calibration resistor $R_{cal}$ and a reference voltage source $U_{Ref}$, wherein the device has a second switching matrix for mutually connecting the terminals of the broadband lambda probe, the grounding resistor $R_{GND}$ and the calibration resistor $R_{cal}$ and the pump current source SQ and the reference current source SQr to a digital measuring system DMS. In that case, provision is made for the first switching matrix to provide the following switching connections:

Z_Off: no switching connection
Z_G0: $R_{GND}$ to SQ
Z_GE: $R_{GND}$ to SQ and RE to SQ
Z_Gi: $R_{GND}$ to SQ and IPE to SQ
Z_Ga: $R_{GND}$ to SQ and APE to SQ
Z_Gi_ai: $R_{GND}$ to SQ, IPE to SQ and APE to SQr
Z_Gi_ei: $R_{GND}$ to SQ, IPE to SQ and RE to SQr
Z_K: $R_{GND}$ to MES and APE to SQ
Z_Ria: APE to SQr and IPE to VM
Z_Rie: RE to SQr and APE to VM
Z_0: IPE to VM
Z_Cal: $R_{cal}$ to SQr
Z_1: $R_{GND}$ to IPE and APE to SQ
Z_2: $R_{GND}$ to APE and IPE to SQ.

Through corresponding circuitry interconnection of the first switching matrix and evaluation of the voltages established, in particular of the voltage drop across the grounding resistor $R_{GND}$, various faults of the broadband lambda probe can be identified. For identifying faults, for example cable breaks in the terminals of the broadband lambda probe, special program sequences are provided in the control unit. These program sequences carry out measurements for identifying various faults of the exhaust gas probe in suitable operating modes of the broadband lambda probe, for example after switch-on (mode SWITCHON) or during the warm-up phase (mode WARMUP).

SUMMARY

It is an object of the present invention to provide a method for identifying cable faults at terminals of a broadband lambda probe.

It is furthermore an object of the invention to provide a corresponding control unit for carrying out the method.

The object of the invention concerning the method is achieved by virtue of the fact that in order to identify the cable faults at least at times a controlled pump current is conducted through the pump cell, and that cable faults are identified by the evaluation of potential swings during the application of the controlled pump current or during a subsequent circuitry interconnection of the broadband lambda probe. In the case of the controlled pump current, the current direction and the current are predetermined rather than regulated as in the case of regular operation of the broadband lambda probe. As a result, defined states are set at the broadband lambda probe or at the terminals of the broadband lambda probe, which enables an unambiguous cable diagnosis. If, by way of example, a load drop is present at the terminals of the pump cell, then the external pump electrode terminal APE and the internal pump electrode terminal IPE are charged to ground or near the supply voltage. Upon suitable subsequent circuitry interconnection of the broadband lambda probe, this leads to an evaluatable potential swing which can then be assigned to a cable break. It is advantageous here that cable faults can also be identified outside separate diagnosis modes during the switch-on or warm-up of the broadband lambda probe. In this case, it is also possible to identify cable breaks in the internal interconnection of the broadband lambda probe.

Preferably, during the subsequent circuitry interconnection the internal pump electrode terminal IPE can be connected to the reference voltage source $U_{Ref}$. In the case of a cable break, for example a break of the external pump electrode terminal APE or of the internal pump electrode terminal IPE, a distinct potential swing thus arises.

In accordance with one preferred configuration variant of the invention it can be provided that during the subsequent circuitry interconnection the reference electrode terminal RE is additionally connected to the reference current source SQr and the pulsed reference pump current is thereby applied to the reference electrode terminal RE, as is possible for example by means of the switching connection Z_Rie. In the case of a cable break and a load drop at the reference electrode terminal RE, this leads to a correspondingly evaluatable charging at said terminal.

Unambiguous identification and assignment of cable breaks of the terminals of broadband lambda probes can be achieved by virtue of the fact that in a controlled pump current operating mode the current direction through the pump cell is predetermined by a switching connection Z_1 or by a switching connection Z_2, in that the internal pump electrode terminal IPE is subsequently connected to the reference voltage source $U_{Ref}$ by a switching connection Z_0, and in that, in the case of a potential swing brought about as a result, a load drop at the internal pump electrode terminal IPE or the external pump electrode terminal APE is deduced.

A simple and cost-effectively implementable identification of cable breaks can be achieved by virtue of the fact that the potential spring is identified by means of an over- or undervoltage identification. In this case, the over- or undervoltage identification can be contained in the control unit or a connected evaluation unit.

It may supplementarily be provided that the voltage drop across the grounding resistor $R_{GND}$ or the voltage $U_{n0}$ between the reference electrode terminal RE and the internal pump electrode terminal IPE is evaluated in addition to the potential swing. By evaluating the voltage drop across the grounding resistor $R_{GND}$ while a controlled pump current is applied to the broadband lambda probe (switching connections Z_1 and Z_2), it is possible to obtain data about defective terminals of the broadband lambda probe and evaluate them in addition to the potential spring determined. If, by way of example, the connecting of the reference voltage source $U_{Ref}$ to the internal pump electrode terminal IPE, on account of a randomly matching potential setting, does not lead to an overvoltage turn-off, the recognition of whether and which terminal of the broadband lambda probe is defective can arise from the evaluation of the voltage drop across the grounding resistor $R_{GND}$. Accordingly, if no unambiguously evaluatable potential swing is present where a pulsed reference current is applied, the voltage $U_{n0}$ between the reference electrode terminal RE and the internal pump electrode terminal IPE can be concomitantly evaluated and it is thereby possible to detect a load drop at the reference electrode terminal RE.

The object of the invention concerning the control unit is achieved by virtue of the fact that the control unit provides a controlled pump current by means of the pump current source SQ for the purpose of monitoring cable faults at the terminals of the broadband lambda probe, in that the controlled pump current is predetermined in a predetermined direction through the pump cell by a switching connection Z_1 or Z_2, that in a subsequent circuitry interconnection in the switching connection Z_0 the internal pump electrode terminal IPE is connected to the reference voltage source $U_{Ref}$ or in the switching connection Z_Rie the reference electrode terminal RE is connected to the reference current source SQr and the internal pump electrode terminal IPE is connected to the reference voltage source $U_{Ref}$, and in that the control unit or an evaluation unit connected to the control unit has measuring means for determining over- and undervoltages as an indicator of cable breaks at the terminals of the broadband lambda probe. The device makes it possible to identify cable breaks at broadband lambda probes outside the operating modes provided therefor, such as are provided, for example, during the switch-on or warm-up of the broadband lambda probe.

BRIEF DESCRIPTION OF THE DRAWINGS

The invention is explained in greater detail below on the basis of an exemplary embodiment illustrated in the figures, in which.

DETAILED DESCRIPTION

Figure 1:
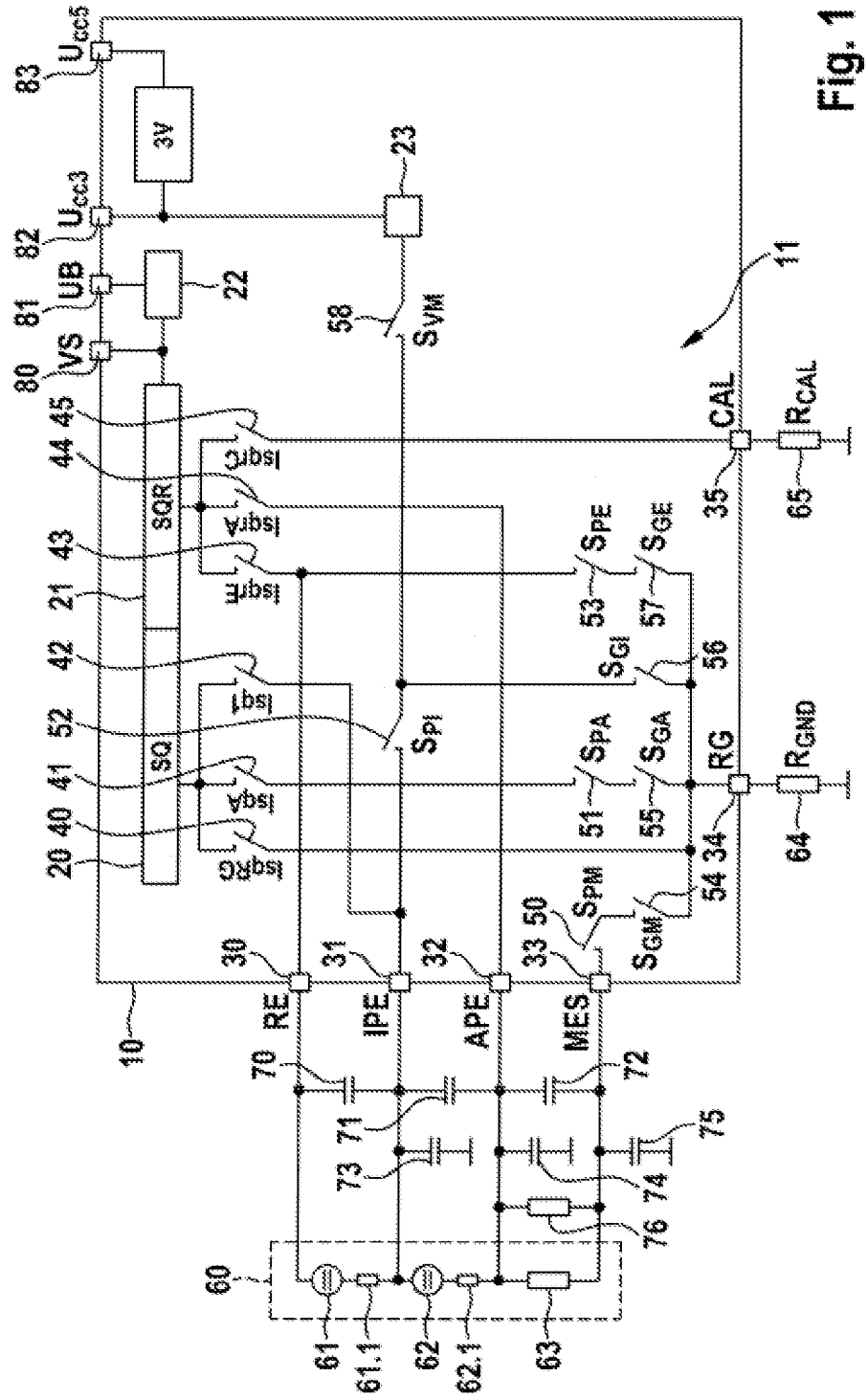
FIG. 1 shows a control unit with a connected broadband lambda probe and a first switching matrix.

FIG. 1 shows, in one exemplary embodiment, a control unit 10 with a connected broadband lambda probe 60 and a first switching matrix 11. In this case, the components and terminals illustrated are reduced to the components and terminals necessary for elucidating the function of the first switching matrix 11. The basic concept, the construction and the basic function of the control unit 10 substantially corresponds to the evaluation and control unit for a broadband lambda probe 60 as presented in the document DE 102008001697 A1 and the as yet unpublished document R.330560 in the name of the present applicant. In this case, the control unit 10 is embodied in the form of an ASIC.

The control unit 10 contains a pump current source SQ 20 and a reference current source SQr 21 for operating the broadband lambda probe 60. Furthermore, a voltage stabilizer 22 and a reference voltage source $U_{Ref}$ 23 are provided.

The voltage supply is effected via a terminal UB 81 (battery voltage), $U_{cc3}$82 (3V voltage supply), and $U_{cc5}$83 (5V voltage supply), and a terminal VS 80 is grounded via a capacitor (not illustrated).

The control unit 10 is connected to the associated terminals of the broadband lambda probe 60 via the terminal RE 30, the terminal IPE 31, the terminal APE 32 and the terminal MES 33. In this case, RE is the terminal of the reference electrode, IPE is the terminal of the internal pump electrode, APE is the terminal of the external pump electrode and MES is a measurement terminal of the broadband lambda probe 60. Furthermore, the control unit 10 is connected to a grounding resistor $R_{GND}$ 64 via a terminal RG 34 and to a calibration resistor $R_{CAL}$ 65 via a terminal CAL 35. The grounding resistor $R_{GND}$ 64 and the calibration resistor $R_{CAL}$ 65 are connected to ground.

The broadband lambda probe 60 is constructed from a Nernst cell 61 and a pump cell 62 in a known form. The equivalent circuit diagram illustrated shows the internal resistance $R_{ire}$ 61.1 of the Nernst cell 61 and the internal resistance $R_{iape}$ 62.1 of the pump cell 62. A resistor $R_{code}$ 63 is provided in a probe plug (not illustrated) of the broadband lambda probe 60. The broadband lambda probe 60 is connected to the control unit 10 via an external circuitry interconnection. In this case, a capacitor C1 70 is provided in parallel with the Nernst cell 60, a capacitor C2 71 is provided in parallel with the pump cell 62 and a capacitor C3 72 and a resistor $R_{mes}$ 76 are provided in parallel with the resistor $R_{code}$ 63. Furthermore, the terminal IPE 31 is connected to ground via a capacitor C4 73, the terminal APE 32 is connected to ground via a capacitor C5 74 and the terminal MES 33 is connected to ground via a capacitor C6 75.

The terminals 30, 31, 32, 33, 34, 35 of the control unit 10, the pump current source SQ 20, the reference current source SQr 21, the terminal $U_{cc3}$ 82 and the reference voltage source $U_{Ref}$ 23 are connected via signal lines of the first switching matrix 11. In this case, the signal lines can be switched via the switches $I_{sqRG}$ 40, $I_{sqA}$ 41, $I_{sqI}$ 42, $I_{sgrE}$ 43, $I_{sqra}$ 44, $I_{sqrC}$ 45, $S_{PM}$50, $S_{pA}$ 51, $S_{pI}$ 52, $S_{PE}$ 53, $S_{GM}$ 54, $S_{GA}$ 55, $S_{GI}$ 56, $S_{GE}$ 57, $S_{VM}$ 58, in a manner driven by a controller (not illustrated).

By means of a suitable position of the switches $I_{sqRG}$ 40, $I_{sqA}$ 41, $I_{sqI}$42, $I_{sqrE}$ 43, $I_{sqrA}$ 44, $I_{sqrC}$ 45, $S_{PM}$ 50, $S_{PA}$ 51, $S_{PI}$ 52, $S_{PE}$ 53, $S_{GM}$ 54, $S_{GA}$ 55, $S_{GI}$ 56, $S_{GE}$ 57, $S_{VM}$58, various signals of the pump current source SQ 20, the reference current source SQr 21 and the reference voltage source $U_{Ref}$ 23 can be applied to the broadband lambda probe 60. From the voltages and voltage profiles established in this case at the terminals RE 30, IPE 31, APE 32, MES 33, RG 34 and CAL 35, it is possible to derive information about the operating state of the broadband lambda probe 60.

In order to determine the operating state, the voltages and voltage profiles established at the respective terminals RE 30, IPE 31, APE 32, MES 33, RG 34 and CAL 35 are conducted by a second switching matrix (not illustrated) likewise in a predeterminable order to a differential amplifier, are amplified there and are subsequently digitized by an analog-to-digital converter connected downstream. The digitized measurement signals can then be fed via a digital interface (not illustrated) to the controller or a superordinate μ-controller for evaluation.

The additional information about the operating state of the broadband lambda probe 60 is measured, depending on the measurement task, in pulse pauses in which the pump cell 62 of the broadband lambda probe 60 is not driven for measuring the oxygen content in the exhaust gas of the internal combustion engine by the pump current source SQ 20, or during the current pulse of the pump current source SQ 20.

Figure 2:
FIG. 2 shows possible switching positions of the first switching matrix.

FIG. 2 shows possible switching positions of the first switching matrix 11, summarized in a table 100. In this case, the first column mentions the designations for the respective switching position, and the first row lists the names of the individual switches introduced in FIG. 1: $I_{sqRG}$ 40, $I_{sqA}$ 41, $I_{sqI}$ 42, $I_{sgrE}$ 43, $I_{sqrA}$ 44, $I_{sqrC}$ 45, $S_{PM}$ 50, $S_{PA}$ 51, $S_{PI}$ 52, $S_{PE}$ 53, $S_{GM}$ 54, $S_{GA}$ 55, $S_{GI}$ 56, $S_{GE}$ 57, $S_{VM}$ 58. The switch positions of the switches $S_{PM}$ 50 and $S_{GM}$ 54, $S_{PA}$ 51 and $S_{GA}$ 55 and $S_{PE}$ 53 and $S_{GE}$ 57 are in each case identical for the switching positions shown and are therefore respectively combined in one column. A zero assigned to a switch $I_{sqRG}$ 40, $I_{sqA}$ 41, $I_{sqI}$ 42, $I_{sgrE}$ 43, $I_{sqrA}$ 44, $I_{sqrC}$ 45, $S_{PM}$ 50, $S_{pA}$ 51, $S_{PI}$ 52, $S_{PE}$ 53, $S_{GM}$54, $S_{GA}$ 55, $S_{GI}$56, $S_{GE}$ 57, $S_{VM}$ 58 means that the switch is open, and a one identifies a closed switch.

In order to detect information about the operating state of the broadband lambda probe 60, successive switching positions of the first switching matrix 11 and of the second switching matrix are switched, wherein the signal conducted via the second switching matrix to the differential amplifier are evaluated.

For the diagnosis of, for example, cable faults in the connections between the control unit 10 and the broadband lambda probe 60, specific diagnosis modes are provided according to known methods, for example during the switch-on (mode SWITCHON) and the warm-up (mode WARMUP) of the broadband lambda probe 60.

The mode SWITCHON is set after the switch-on or after a fault case for the start-up of the broadband lambda probe 60. By means of corresponding switching connections of the first switching matrix 11 and of the second switching matrix, fault current measurements for identifying shunts and short circuits with respect to the probe lines are carried out, inter alia.

The mode WARMUP is set if the probe temperature is so low that the pump current cannot yet be set, or if, after fault messages, short circuits are intended to be distinguished from cable interruptions. In this case, too, the diagnosis of the cable connections is effected by means of corresponding switch positions of the first switching matrix 11 and second switching matrix.

The invention provides for using a set pump current for the diagnosis of cable faults, in particular of load drops on the cable lines between the broadband lambda probe 60 and the control unit 10. Depending on the measured signals, in addition the pulsed reference pump current can concomitantly be utilized. As a result, an unambiguous determination and assignment of cable breaks is possible, including outside the diagnosis modes mentioned.

Thus, by way of example, a cable diagnosis can be carried out during a mode Normal 1 or a mode Normal 2. The mode Normal 1 is set if the probe temperature suffices to set the pump current. The mode Normal 2 is set if the charge reversal correction is intended to be calibrated.

By mans of the controlled pump current it is possible to determine, for example, cable breaks on the lines RE, IPE and APE-S. In this case, APE-S denotes a break of the feed line to the external pump electrode within the broadband lambda probe 60. In order to set the controlled pump current, the broadband lambda probe 60 is connected to the pump current source SQ 20 by means of the first switching matrix 11 in such a way that only one of the two energization directions possible in principle is constrained. This is brought about by means of the switching connections Z_1 and Z_2 in the exemplary embodiment shown. Alternatively, the circuitry interconnection can also be effected in such a way that no effective pump current flows, pulse and couter-pulse furthermore being present.

During the measurement, the pulsed reference pump current is completely switched off in order to avoid side effects.

If a load drop is present at APE-S or IPE, then during the switching connection Z_1 or Z_2 the terminal APE 32 and the terminal IPE 31 are in any case charged by the pump current to values close to ground and close to battery voltage respectively. If, in a subsequent circuitry interconnection, the terminal IPE 31 is connected by the switching connection Z_0 to the reference voltage source $U_{Ref}$ 23 and thus connected to a virtual ground (3.3V), a sudden potential swing results. The latter can be detected by means of an over- or undervoltage identification. Since there are only a limited number of causes of over- or undervoltage faults, an assignment to the cable faults mentioned is possible.

If the connecting of the virtual ground by a randomly matching potential setting does not result in an over- or undervoltage switch-off, the cable faults can also be identified by means of a corresponding evaluation of the voltage drop across the grounding resistor $R_{GND}$. This shows that one of the load drops APE-S or IPE exists. A distinction between the two load drops mentioned can be made by means of measurements that were already performed in the modes WARMUP and SWITCHON.

If no load drop can be detected on the lines APE-S and IPE, the pulsed reference pump current can additionally be switched in. In the exemplary embodiment shown, this is effected by means of the switching connection Z_Rie. In the case of a load drop at the terminal of the reference electrode, charging takes place at the terminal RE 30 with a corresponding over- or undervoltage identification. In this case, too, it is additionally possible to detect a cable fault by evaluation of, for example, the voltage $U_{n0}$ between the terminal RE 30 and the terminal IPE 31, if the over- or undervoltage identification does not respond.

The invention has made it possible, by using a controlled pump current operating mode in conjunction with a matching setting of the pulsed reference pump current, to unambiguously detect cable faults in leads of the broadband lambda probe 60 and to assign them to the respective terminal. In this case, the cable diagnosis is not restricted to separate diagnosis modes during the switch-on and warm-up of the broadband lambda probe 60.

What is claimed is:

1. A method for identifying cable faults at the terminals of a broadband lambda probe (60) comprising a Nernst cell (61) and a pump cell (62) in an exhaust gas duct of an internal combustion engine, wherein the broadband lambda probe (60) has a reference electrode terminal RE, an internal pump electrode terminal IPE and an external pump electrode terminal APE, wherein, via a control unit (10), a pump current is applied to the broadband lambda probe (60) by a pump current source SQ (20) and a pulsed reference pump current is applied to the broadband lambda probe (60) by a reference current source SQr (21), wherein the pump current source SQ (20) and the reference current source SQr (21) are mutually connected to the terminals of the broadband lambda probe (60), a grounding resistor $R_{GND}$ (64) and a reference voltage source $U_{Ref}$(23) with the aid of a first switching matrix (11) and wherein the first switching matrix (11) enables at least the switching connections:

Z_1: $R_{GND}$ with IPE and APE with SQ
Z_2: $R_{GND}$ with APE and IPE with SQ
Z_0: IPE with VM Z_Rie: RE with SQr and IPE with VM, characterized in that in order to identify the cable faults at least at times a controlled pump current is conducted through the pump cell (62), and in that cable faults are identified by the evaluation of potential swings of the current.

2. The method according to claim 1, characterized in that the potential swings are evaluated during the application of the controlled pump current.

3. The method according to claim 1, characterized in that the potential swings are evaluated during a subsequent circuitry interconnection of the broadband lambda probe (60).

4. The method according to claim 1, characterized in that during the subsequent circuitry interconnection the internal pump electrode terminal IPE is connected to the reference voltage source $U_{Ref}$(23).

5. The method according to claim 4, characterized in that during the subsequent circuitry interconnection the reference electrode terminal RE is additionally connected to the reference current source SQr (21) and the pulsed reference pump current is thereby applied to the reference electrode terminal RE.

6. The method according to claim 1, characterized in that in a controlled pump current operating mode the current direction through the pump cell (62) is predetermined by a switching connection, in that the internal pump electrode terminal IPE is subsequently connected to the reference voltage source $U_{Ref}$(23) by a switching connection Z_0, and in that, in the case of a potential swing brought about as a result, a load drop is deduced.

7. The method according to claim 6, characterized in that the current direction through the pump cell (62) is predetermined by a switching connection Z_1.

8. The method according to claim 6, characterized in that the current direction through the pump cell (62) is predetermined by a switching connection Z_2.

9. The method according to claim 6, characterized in that the load drop is at the internal pump electrode terminal IPE.

10. The method according to claim 6, characterized in that the load drop is at or the external pump electrode terminal APE.

11. The method according to claim 1, characterized in that the potential swing is identified by an over- or undervoltage identification.

12. The method according to claim 1, characterized in that a voltage drop across the grounding resistor $R_{GND}$ (64) is evaluated in addition to the potential swing.

13. The method according to claim 1, characterized in that a voltage $U_{n0}$ between the reference electrode terminal RE and the internal pump electrode terminal IPE is evaluated in addition to the potential swing.

14. A control unit (10) for operating a broadband lambda probe (60) comprising a Nernst cell (61) and a pump cell (62) in an exhaust gas duct of an internal combustion engine and for detecting information about the operating state of the broadband lambda probe, wherein the broadband lambda probe (60) has as terminals a reference electrode terminal RE, an internal pump electrode terminal IPE and an external pump electrode terminal APE, wherein the control unit (10) is connected to the terminals of the broadband lambda probe (60) and a grounding resistor $R_{GND}$ (64) and a calibration resistor $R_{cal}$ (65) wherein the control unit (10) has a first switching matrix (11) for mutually connecting a pump current source SQ (20) and a reference current source SQr (21) to the terminals of the broadband lambda probe, the grounding resistor $R_{GND}$ (64), the calibration resistor $R_{cal}$ (65) and a reference voltage source $U_{Ref}$(23), wherein the control unit (10) has a second switching matrix for mutually connecting the terminals of the broadband lambda probe (60), the grounding resistor $R_{GND}$ (64) and the calibration resistor $R_{cal}$ (65), and the pump current source SQ (20) and the reference current source SQr (21) to a digital measuring system DMS, and wherein the first switching matrix (11) provides at least the following switching connections:

Z_1: $R_{GND}$ with IPE and APE with SQ
Z_2: $R_{GND}$ with APE and IPE with SQ
Z_0: IPE with VM
Z_Rie: RE with SQr and IPE with VM, characterized in that the control unit (10) provides a controlled pump current by the pump current source SQ (20) for the purpose of monitoring cable faults at the terminals of the broadband lambda probe (60), in that the controlled pump current is predetermined in a predetermined direction through the pump cell (62) by a switching connection, in that in a subsequent circuitry interconnection in the switching connection Z_0 the internal pump electrode terminal IPE is connected to the reference voltage source $U_{Ref}$ (23) or in the switching connection Z_Rie the reference electrode terminal RE is connected to the reference current source SQr (21) and the internal pump electrode terminal IPE is connected to the reference voltage source $U_{Ref}$ (23), and in that a measuring means determines over- and undervoltages as an indicator of cable breaks at the terminals of the broadband lambda probe (60).

15. The control unit according to claim 14, characterized in that the controlled pump current is predetermined in a predetermined direction through the pump cell (62) by a switching connection Z_1.

16. The control unit according to claim 14, characterized in that the controlled pump current is predetermined in a predetermined direction through the pump cell (62) by a switching connection Z_2.

17. The control unit according to claim 14, characterized in that the control unit (10) includes the measuring means.

18. The control unit according to claim 14, characterized in that an evaluation unit connected to the control unit (10) includes the measuring means.

* * * * *